US012119761B2

(12) United States Patent
Kanetaka et al.

(10) Patent No.: US 12,119,761 B2
(45) Date of Patent: Oct. 15, 2024

(54) INJECTOR AND CONTROL METHOD FOR AN ULTRASONIC MOTOR

(71) Applicant: NEMOTO KYORINDO CO., LTD., Tokyo (JP)

(72) Inventors: Toshio Kanetaka, Tokyo (JP); Makoto Udagawa, Tokyo (JP); Toshiiku Sashida, Tokyo (JP)

(73) Assignee: NEMOTO KYORINDO CO., LTD., Tokyo (JP)

( * ) Notice: Subject to any disclaimer, the term of this patent is extended or adjusted under 35 U.S.C. 154(b) by 0 days.

(21) Appl. No.: 17/654,392

(22) Filed: Mar. 10, 2022

(65) Prior Publication Data

US 2022/0200487 A1    Jun. 23, 2022

Related U.S. Application Data

(60) Continuation of application No. 15/355,969, filed on Nov. 18, 2016, now Pat. No. 11,303,227, which is a
(Continued)

(30) Foreign Application Priority Data

Jun. 14, 2011    (JP) ................................. 2011-132031

(51) Int. Cl.
*B05B 17/06*    (2006.01)
*A61M 5/00*    (2006.01)
(Continued)

(52) U.S. Cl.
CPC .............. *H02N 2/14* (2013.01); *A61M 5/007* (2013.01); *A61M 5/14546* (2013.01);
(Continued)

(58) Field of Classification Search
CPC .......... B05B 1/14; B05B 17/06; F02M 61/18; F02M 7/06; F02M 35/10216; F02M 61/1826; F02M 35/1216; F02D 9/109
(Continued)

(56) References Cited

U.S. PATENT DOCUMENTS 3,323,763 A  *  6/1967  Butts ....................... F16F 1/387
                                                 248/606
3,860,300 A  *  1/1975  Lyman ................ F16C 32/0476
                                                 310/90.5
(Continued)

FOREIGN PATENT DOCUMENTS

CN           1871041 A      11/2006
CN         101702592 A       5/2010
(Continued)

OTHER PUBLICATIONS

An Office Action; "Notice of Reasons for Refusal", mailed by the Japanese Patent Office on Aug. 3, 2021, which corresponds to Japanese Patent Application No. 2019-152479 and is related to U.S. Appl. No. 15/355,969 ; with English language translation.
(Continued)

*Primary Examiner* — Chee-Chong Lee
(74) *Attorney, Agent, or Firm* — Studebaker & Brackett PC

(57) ABSTRACT

Provided is an injector in which adhesion between a stator and a rotor of an ultrasonic motor can be released efficiently. An injector (1) which injects a chemical liquid includes: an ultrasonic motor unit (3) including an ultrasonic motor (31); a drive mechanism (4) to be driven by the ultrasonic motor unit (3) so as to feed the chemical liquid when the ultrasonic motor (31) rotates forwardly; and a control device (5) which controls the ultrasonic motor (31) of the ultrasonic motor unit (3). The ultrasonic motor (31) includes a stator (32) and a rotor (33), and the control device (5) controls the ultrasonic
(Continued)

motor (31) to alternately repeat forward rotation and reverse rotation so that adhesion between the stator (32) and the rotor (33) is released.

8 Claims, 9 Drawing Sheets

Related U.S. Application Data division of application No. 14/126,364, filed as application No. PCT/JP2012/003730 on Jun. 7, 2012, now Pat. No. 9,545,646.

(51) Int. Cl.
*A61M 5/145* (2006.01)
*H02N 2/06* (2006.01)
*H02N 2/12* (2006.01)
*H02N 2/14* (2006.01)
*H02N 2/16* (2006.01)

(52) U.S. Cl.
CPC ............ *B05B 17/06* (2013.01); *H02N 2/062* (2013.01); *H02N 2/126* (2013.01); *H02N 2/163* (2013.01); *H02N 2/166* (2013.01); *A61M 5/1452* (2013.01); *A61M 2205/058* (2013.01)

(58) Field of Classification Search
USPC .................................................. 239/102.1, 5
See application file for complete search history.

(56) References Cited

U.S. PATENT DOCUMENTS

| | | | | |
|---|---|---|---|---|
| 3,874,778 | A | * | 4/1975 | Kato .................. G02B 7/18 359/200.1 |
| 3,955,858 | A | * | 5/1976 | Poubeau .............. B64G 1/36 310/90.5 |
| 4,285,251 | A | * | 8/1981 | Swartout ............. F16F 15/305 474/196 |
| 4,325,264 | A | | 4/1982 | Sashida |
| 4,444,444 | A | * | 4/1984 | Benedetti ............. H02K 7/09 310/90.5 |
| 4,786,344 | A | | 11/1988 | Beuther |
| 5,041,132 | A | * | 8/1991 | Miyata ............... A61M 60/454 310/317 |
| 5,264,930 | A | | 11/1993 | Florence et al. |
| 5,404,013 | A | | 4/1995 | Tajima |
| 5,679,384 | A | | 10/1997 | Emoto |
| 6,211,604 | B1 | | 4/2001 | Oda et al. |
| 6,262,505 | B1 | * | 7/2001 | Hockney ............. H02K 7/083 310/90.5 |
| 6,464,663 | B1 | | 10/2002 | Zinger |
| 6,707,233 | B2 | | 3/2004 | Oda et al. |
| 6,929,619 | B2 | | 8/2005 | Fago et al. |
| 7,234,928 | B2 | | 6/2007 | Emoto et al. |
| 7,553,294 | B2 | | 6/2009 | Lazzaro et al. |
| 7,960,884 | B2 | | 6/2011 | Miyata et al. |
| 2003/0028144 | A1 | | 2/2003 | Duchon et al. |
| 2004/0193328 | A1 | | 9/2004 | Zaitsu et al. |
| 2006/0082253 | A1 | | 4/2006 | Hara |
| 2007/0093712 | A1 | | 4/2007 | Nemoto et al. |
| 2008/0219088 | A1 | | 9/2008 | Wood et al. |
| 2014/0340002 | A1 | | 11/2014 | Nishimoto |

FOREIGN PATENT DOCUMENTS

| | | |
|---|---|---|
| JP | S64-50690 U | 3/1989 |
| JP | H03-018280 A | 1/1991 |
| JP | H03-284176 A | 12/1991 |
| JP | H05-084296 A | 4/1993 |
| JP | H05-344760 A | 12/1993 |
| JP | H06-054557 A | 2/1994 |
| JP | H06-253200 A | 9/1994 |
| JP | H07-115783 A | 5/1995 |
| JP | H07-250488 A | 9/1995 |
| JP | H08-140371 A | 5/1996 |
| JP | H10-098891 A | 4/1998 |
| JP | H11-191969 A | 7/1999 |
| JP | H11-191970 A | 7/1999 |
| JP | 2000-156986 A | 6/2000 |
| JP | 2001-359286 A | 12/2001 |
| JP | 2002-034214 A | 1/2002 |
| JP | 2004-024476 A | 1/2004 |
| JP | 2006-025573 A | 1/2006 |
| JP | 2006-115631 A | 4/2006 |
| JP | 2006-334890 A | 12/2006 |
| JP | 2009-033946 A | 2/2009 |
| WO | 2005/039675 A1 | 5/2005 |
| WO | 2008/004669 A1 | 1/2008 |

OTHER PUBLICATIONS

An Office Action; "Notice of Reasons for Refusal", mailed by the Japanese Patent Office on Nov. 17, 2020 which corresponds to Japanese Patent Application No. 2019-152479 and is related to U.S. Appl. No. 15/355,969; with English language translation.
An Office Action mailed by China National Intellectual Property Administration on Sep. 3, 2020, which corresponds to Chinese Application No. 201811338593.7 and is related to U.S. Appl. No. 15/355,969 with English language translation.
An Office Action mailed by the Japan Patent Office on Feb. 21, 2019, which corresponds to Japanese Patent Application No. 2017-212525 and is related to U.S. Appl. No. 15/355,969; with English translation.
An Office Action mailed by the Japanese Patent Office on Dec. 11, 2018, which corresponds to Japanese Patent Application No. 2017-212525 and is related to U.S. Appl. No. 15/355,969; with English translation.
CN Office Action dated Nov. 16, 2017, from corresponding CN Appl No. 2015106718710, with English translation, 13 pp.
An Office Action; "Notification of Reasons for Refusal," issued by the Japanese Patent Office on Aug. 23, 2016, which corresponds to Japanese Patent Application No. 2015-182462 and is related to U.S. Appl. No. 14/126,364; with English language translation.
An Office Action; "Notification of Reasons for Refusal," issued by the Japanese Patent Office on Jul. 25, 2011, which corresponds to Japanese Patent Application No. 2011-132031 and is related to U.S. Appl. No. 14/126,364; with English language translation.
An Office Action; "Notification of Reasons for Refusal," issued by the Japanese Patent Office on Oct. 19, 2011, which corresponds to Japanese Patent Application No. 2011-132031 and is related to U.S. Appl. No. 14/126,364; with English language translation.
An Office Action; "Notification of Reasons for Refusal," issued by the Japanese Patent Office on Mar. 3, 2015, which corresponds to Japanese Patent Application No. 2012-002660 and is related to U.S. Appl. No. 14/126,364; with English language translation.
International Search Report; PCT/JP2012/003730; Sep. 11, 2012.
Written Opinion of the International Searching Authority; PCT/JP2012/003730; Sep. 11, 2012.

* cited by examiner

INJECTOR AND CONTROL METHOD FOR AN ULTRASONIC MOTOR

CROSS-REFERENCE TO RELATED APPLICATIONS

This application is a Continuation application of U.S. patent application Ser. No. 15/355,969 filed on Nov. 18, 2016, which is a Divisional application of U.S. patent application Ser. No. 14/126,364 filed on Dec. 13, 2013, which is a U.S. National Phase application of International Patent Application No. PCT/JP2012/003730, filed on Jun. 7, 2012, claims priority to and the benefit of Japanese Patent Application No. 2011-132031 filed on Jun. 14, 2011, the entire contents of which are incorporated herein by reference.

TECHNICAL FIELD

The present invention relates to an injector for injecting a chemical liquid, which includes an ultrasonic motor and is capable of releasing adhesion between a stator and a rotor of the ultrasonic motor. Further, the present invention relates to a control method for an ultrasonic motor.

BACKGROUND ART

Conventionally, as a medical injector for injecting a chemical liquid such as a contrast medium, there has been known an injector including an ultrasonic motor made of a non-magnetic material (Patent Literature 1). This injector is free from trouble due to a magnetic flux, and is therefore usable in combination with an apparatus utilizing a magnetic field, such as a magnetic resonance imaging (MRI) apparatus.

CITATION LIST

Patent Literature

PTL 1: Japanese Patent Application Laid-Open No. 5-84296

SUMMARY OF INVENTION

Technical Problem

In this injector, a stator and a rotor of the ultrasonic motor are constantly held in press contact with each other. Therefore, in a stopped state of the ultrasonic motor, the stator and the rotor may adhere to each other. Particularly in a high-humidity environment, the adhesion is more likely to occur as compared to a normal environment. When the stator and the rotor adhere to each other, the ultrasonic motor cannot be driven. As a result, there is a risk that the chemical liquid cannot be injected.

Solution to Problem

In order to solve the above-mentioned problem, according to an exemplary embodiment of the present invention, there is provided an injector which injects a chemical liquid, the injector including: an ultrasonic motor unit including an ultrasonic motor; a drive mechanism to be driven by the ultrasonic motor unit so as to feed the chemical liquid when the ultrasonic motor rotates forwardly; a control device which controls the ultrasonic motor of the ultrasonic motor unit, wherein the ultrasonic motor includes a stator and a rotor, and the control device controls the ultrasonic motor to alternately repeat forward rotation and reverse rotation so that adhesion between the stator and the rotor is released.

Accordingly, the adhesion between the stator and the rotor of the ultrasonic motor can be released efficiently. Therefore, the drive of the ultrasonic motor can be maintained, and hence the chemical liquid can be injected stably. Further, the control device of the injector automatically releases the adhesion, with the result that the step of determining the presence/absence of the adhesion by the control device can be omitted, and the time and effort of the user for releasing the adhesion can be saved as well.

Further, according to an exemplary embodiment of the present invention, there is provided a control method for an ultrasonic motor which is provided in an ultrasonic motor unit driving a drive mechanism, and which includes a stator and a rotor, the control method including: controlling the ultrasonic motor to alternately repeat forward rotation and reverse rotation so that adhesion between the stator and the rotor is released.

Accordingly, the adhesion between the stator and the rotor of the ultrasonic motor can be released efficiently. Therefore, the drive of the ultrasonic motor can be maintained. Further, the ultrasonic motor is controlled so that the adhesion is automatically released, with the result that the step of determining the presence/absence of the adhesion can be omitted, and the time and effort of the user for releasing the adhesion can be saved as well.

Further, according to an exemplary embodiment of the present invention, there is provided an injector which injects a chemical liquid, the injector including: an ultrasonic motor unit including an ultrasonic motor; a drive mechanism to be driven by the ultrasonic motor unit so as to feed the chemical liquid when the ultrasonic motor rotates forwardly; and a control device for controlling the ultrasonic motor of the ultrasonic motor unit, wherein the ultrasonic motor includes a stator and a rotor, and the control device controls the ultrasonic motor to alternately repeat forward rotation and reverse rotation multiple times within a preset time period so that adhesion between the stator and the rotor is released, and controls the ultrasonic motor to stop for a predetermined time period between the forward rotation and the reverse rotation, and the control device controls the ultrasonic motor so that, when the forward rotation and the reverse rotation are repeated multiple times, a predetermined stopping time period is provided after a preceding operation including forward rotation and reverse rotation, and before a succeeding operation including forward rotation and reverse rotation and performed subsequently to the preceding operation.

Further, according to an exemplary embodiment of the present invention, there is provided a control method for an ultrasonic motor which is provided in an ultrasonic motor unit driving a drive mechanism to be used for an injector that injects a chemical liquid, and which includes a stator and a rotor, the control method including: controlling the ultrasonic motor to alternately repeat forward rotation and reverse rotation multiple times within a preset time period so that adhesion between the stator and the rotor is released, and to stop for a predetermined time period between the forward rotation and the reverse rotation, so that, when the forward rotation and the reverse rotation are repeated multiple times, a predetermined stopping time period is provided after a preceding operation including forward rotation and reverse rotation, and before a succeeding operation including forward rotation and reverse rotation and performed subsequently to the preceding operation.

Further features of the present invention will become apparent from the following description of exemplary embodiments with reference to the attached drawings.

DESCRIPTION OF EMBODIMENTS

Hereinafter, an exemplary embodiment for carrying out the present invention is described in detail with reference to the drawings. Note that, dimensions, materials, shapes, relative positions of components, and the like to be described in the following embodiment are provided arbitrarily, and may be changed depending on the configuration of an apparatus to which the present invention is applied, or various conditions. Unless otherwise noted, the scope of the present invention is not limited to a mode specifically described in the following embodiment.

Embodiment

Figure 1:
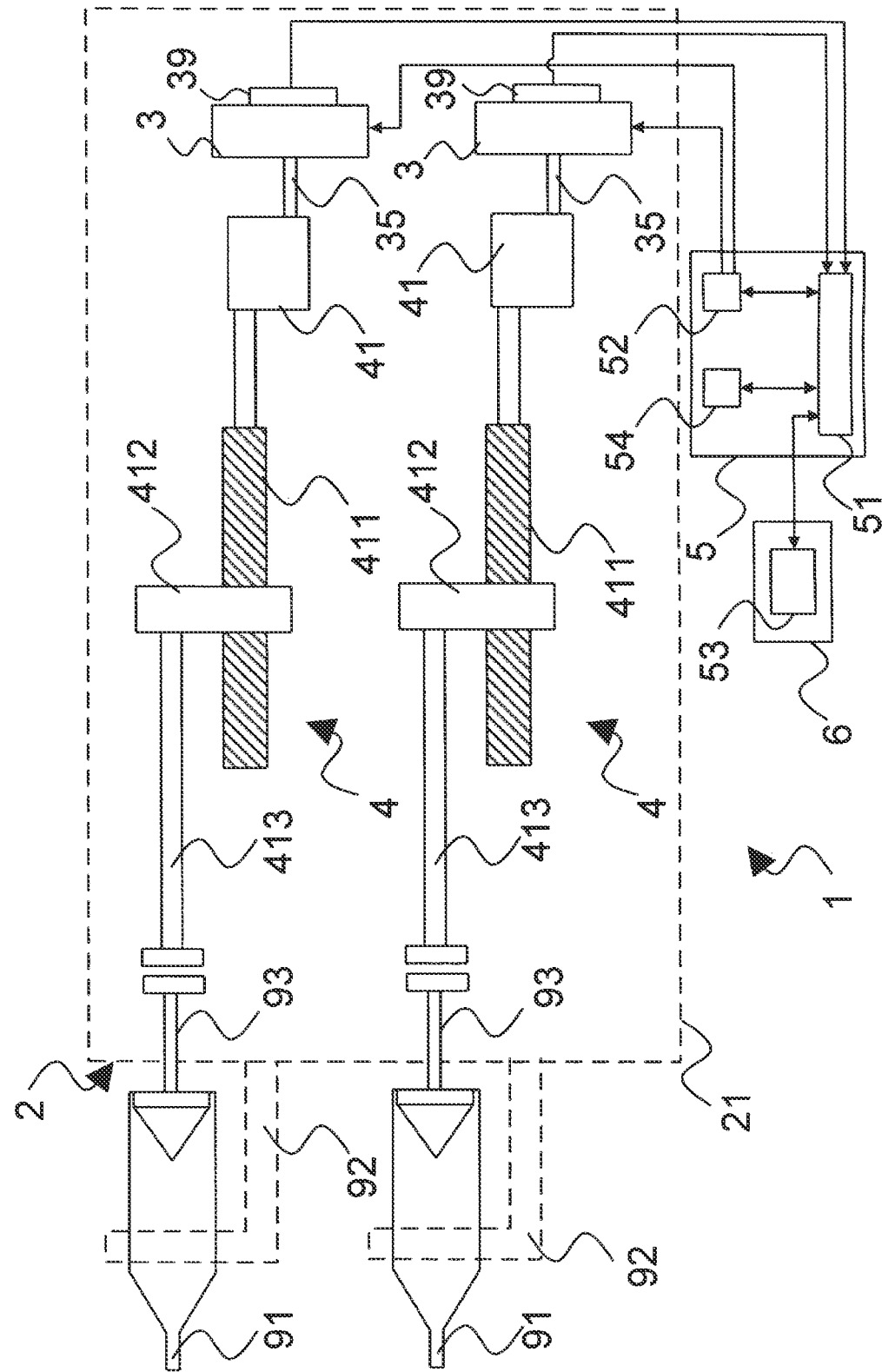
FIG. 1 is a block diagram of an injector.
Figure 2:
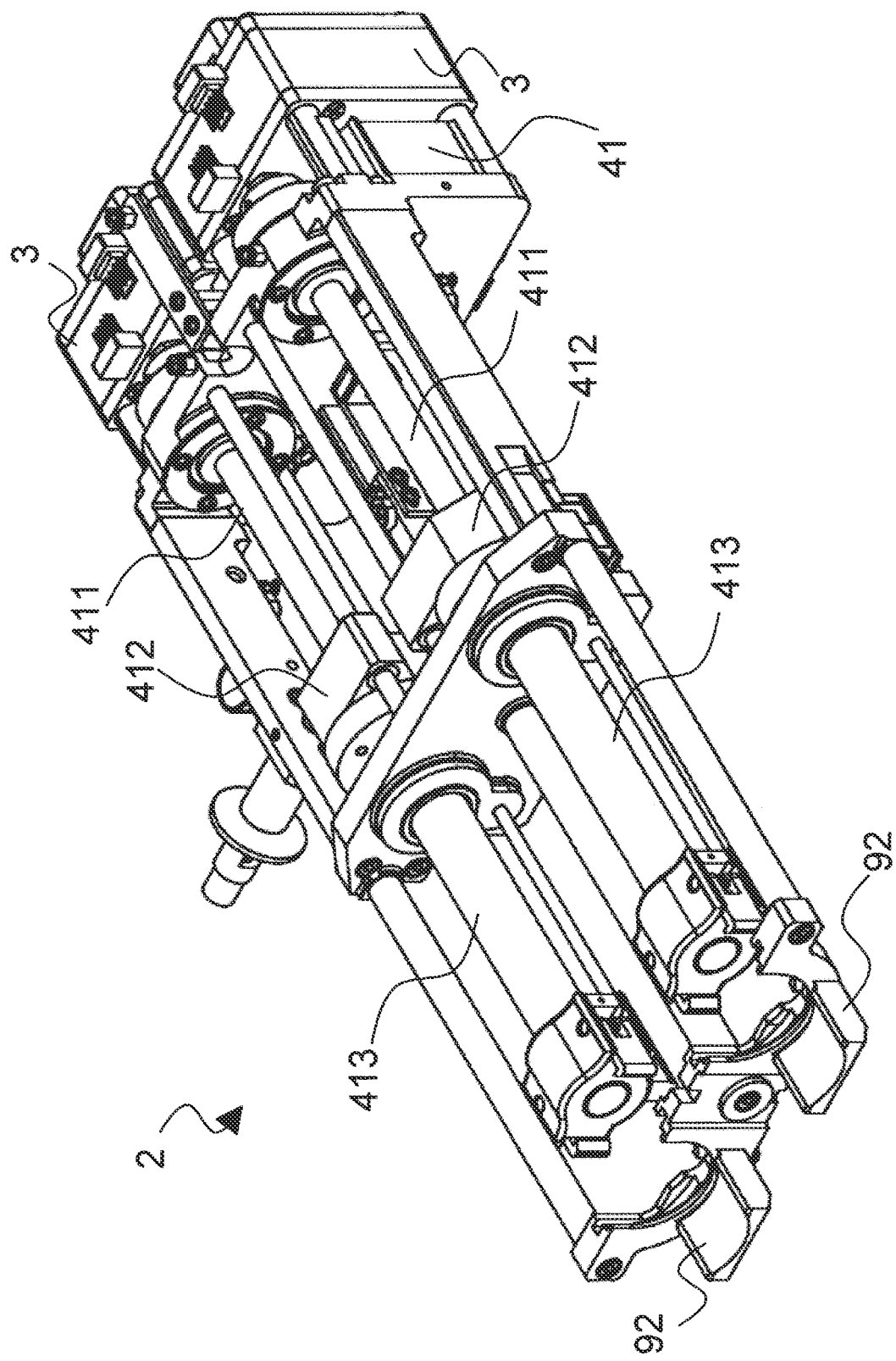
FIG. 2 is a schematic perspective view of an injection head.

FIG. 1 is a block diagram of an injector 1 according to this embodiment. FIG. 2 is a schematic perspective view of an injection head 2 according to this embodiment. The injection head 2 may be mounted to a stand (not shown) or a ceiling suspension device (not shown). In FIG. 2, for convenience of the description, the injection head 2 is illustrated in a state in which part of a frame 21 is removed.

As illustrated in FIG. 1, the injector 1 for injecting a chemical liquid includes an ultrasonic motor unit 3 including an ultrasonic motor 31, a drive mechanism 4 to be driven by the ultrasonic motor unit 3 so as to feed the chemical liquid when the ultrasonic motor 31 rotates forwardly, and a control device 5 for controlling the ultrasonic motor 31 of the ultrasonic motor unit 3. The drive mechanism 4 and the ultrasonic motor unit 3 are housed in the frame 21 of the injection head 2 of the injector 1. The frame 21 includes two syringe holders 92 for holding two cylinders 91. The injector 1 includes a console 6 including a display 53 for displaying an injection status of a chemical liquid and the like. The console 6 is connected to the control device 5 via such as an optical cable, and the control device 5 is connected to the injection head 2. Through the connection between the console 6 and the control device 5 via the optical cable, adverse effects due to noise can be reduced. The control device 5 and the console 6 are connected to an external power supply provided inside an examination room or outside the examination room, and the control device 5 also functions as a power supply.

The control device 5 includes a CPU 51 for controlling the ultrasonic motor unit 3, a drive circuit 52 for applying a voltage to the ultrasonic motor unit 3, and a timer 54 for measuring a rotation time period of the ultrasonic motor 31 or an injection time period of the chemical liquid. The CPU 51 is electrically connected to the drive circuit 52 so as to transmit a drive signal to the ultrasonic motor unit 3, and the drive circuit 52 is electrically connected to the ultrasonic motor unit 3. An encoder 39 is connected to the ultrasonic motor unit 3, and transmits, to the control device 5, information on the number of rotations of the ultrasonic motor 31 and the presence/absence of the rotation. When assuming that a front side corresponds to the side in the frame 21 on which the syringe holder 92 is situated, the ultrasonic motor unit 3 is arranged at a rear side portion.

The drive mechanism 4 is arranged between the syringe holder 92 and the ultrasonic motor unit 3. The drive mechanism 4 includes a transmission mechanism 41 connected to a shaft 35 of the ultrasonic motor unit 3, a ball screw shaft 411 connected to the transmission mechanism 41, a ball screw nut 412 mounted to the ball screw shaft 411, and an actuator 413 connected to the ball screw nut 412. The ball screw nut 412 is threadedly engaged in the middle of the ball screw shaft 411. The transmission mechanism 41 transmits the rotation from the ultrasonic motor unit 3 to the ball screw shaft 411. The transmission mechanism 41 includes a pinion gear connected to the shaft 35, and a screw gear connected to the ball screw shaft 411. The rotation of the shaft 35 of the ultrasonic motor unit 3 is transmitted to the ball screw shaft 411 via the pinion gear and the screw gear. Accordingly, the ball screw shaft 411 rotates in accordance with the transmitted rotation. The ball screw nut 412 slides in a forward direction (front side direction) or a backward direction (rear side direction) along with the rotation of the ball screw shaft 411. As a result, along with the slide of the ball screw nut 412, the actuator 413 moves forwardly or backwardly. That is, when the shaft 35 rotates forwardly, the actuator 413 moves forwardly, and when the shaft 35 rotates reversely, the actuator 413 moves backwardly.

When injecting the chemical liquid, the cylinder 91 filled with the chemical liquid is mounted to the syringe holder 92. A piston 93 slidable in the cylinder 91 is fitted to the cylinder 91. The cylinder 91 is mounted so that a rod of the piston 93 abuts against a distal end of the actuator 413. Accordingly, when the ball screw nut 412 slides in the forward direction under a state in which the cylinder 91 is mounted, the actuator 413 presses the piston 93 in the forward direction. When the piston 93 moves forwardly, the chemical liquid is ejected from the cylinder 91, and is injected into the body of a patient via such as a catheter connected to a distal end of the cylinder 91. When the ball screw nut 412 slides in the backward direction, the actuator 413 draws the piston 93 in the backward direction.

In a case of injecting the chemical liquid, the user mounts the cylinder 91 to the syringe holder 92, and turns ON the injector 1. In a case where the display 53 is a touch panel, the user then presses an injection button displayed on the touch panel. In a case where an operation unit is provided to the injection head 2, the user may press an injection button of the operation unit. When the injection button is pressed, the control device 5 transmits a forward rotation signal as the drive signal to the ultrasonic motor unit 3. In response to the forward rotation signal, the ultrasonic motor 31 in the ultrasonic motor unit 3 is driven, and the shaft 35 rotates forwardly. When the shaft 35 rotates forwardly, the encoder 39 detects the rotation and transmits a pulse signal to the control device 5. In a case where the injection is finished and the cylinder 91 is to be removed, the control device 5 transmits a reverse rotation signal as the drive signal to the ultrasonic motor unit 3 so that the piston 93 is moved backwardly. In response to the reverse rotation signal, the ultrasonic motor 31 in the ultrasonic motor unit 3 is driven, and the shaft 35 rotates reversely. The drive signal transmitted to the ultrasonic motor unit is an alternating current signal. When assuming that the forward rotation signal corresponds to a case where, of two types of signals different in phase, one of the signals is delayed relative to another of the signals, the reverse rotation signal corresponds to a case where the other of the signals is delayed relative to the one of the signals.

The control device 5 previously stores an injection protocol, and the injection of the chemical liquid is performed automatically in accordance with the injection protocol. A storage medium having the injection protocol stored thereon may be inserted into the control device 5 so that the injection of the chemical liquid is performed in accordance with the injection protocol read from the storage medium. At the time of normal control performed in accordance with the injection protocol, a normal voltage within a preset range is applied from the drive circuit 52 to the ultrasonic motor unit 3. In the injection protocol, there are set, for example, an injection time period, an injection rate, an injection amount, and an injection pressure limit value. The contents of the injection protocol are displayed on the display 53, and hence the user can confirm the contents of the injection protocol. The control device 5 uses the timer 54 to control the injection time period. Further, the control device 5 monitors the injection status, and when abnormality, such as decrease in injection pressure, is detected, the control device 5 automatically stops the injection of the chemical liquid. The injection pressure can be detected using a load cell provided at the distal end of the actuator 413.

In FIG. 1, the control device 5 and the console 6 are provided independently of each other, but the control device 5 and the console 6 may alternatively be provided integrally with each other. The control device 5 is arranged outside the frame 21 of the injection head 2, but may alternatively be arranged inside the frame 21. Further, the control device 5 and the console 6 may be provided integrally with the injection head 2. Further, the control device 5 and the console 6 may be configured to communicate to each other through radio communication or infrared communication.

Figure 3:
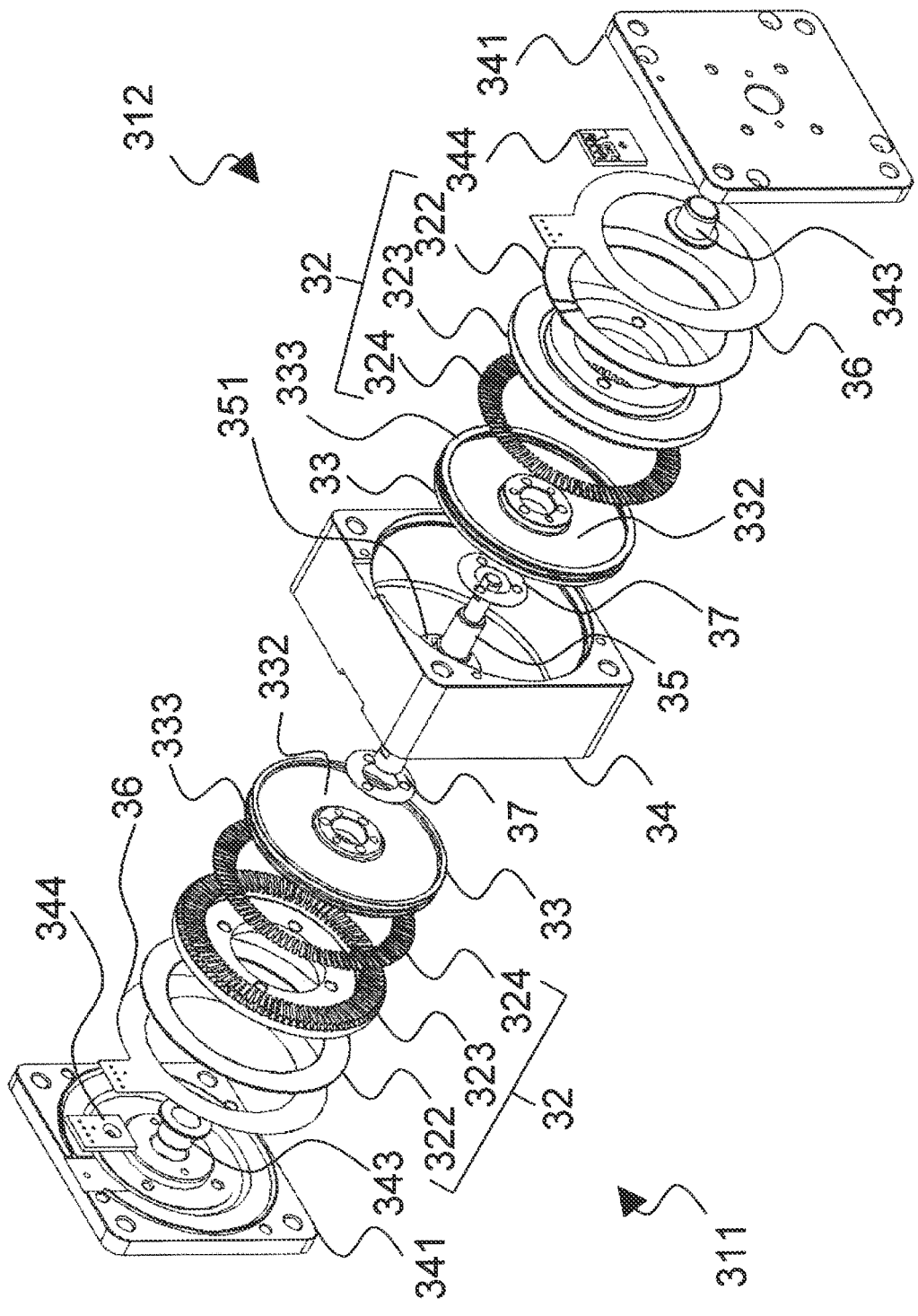
FIG. 3 is a schematic developed view of an ultrasonic motor unit.
Figure 4:
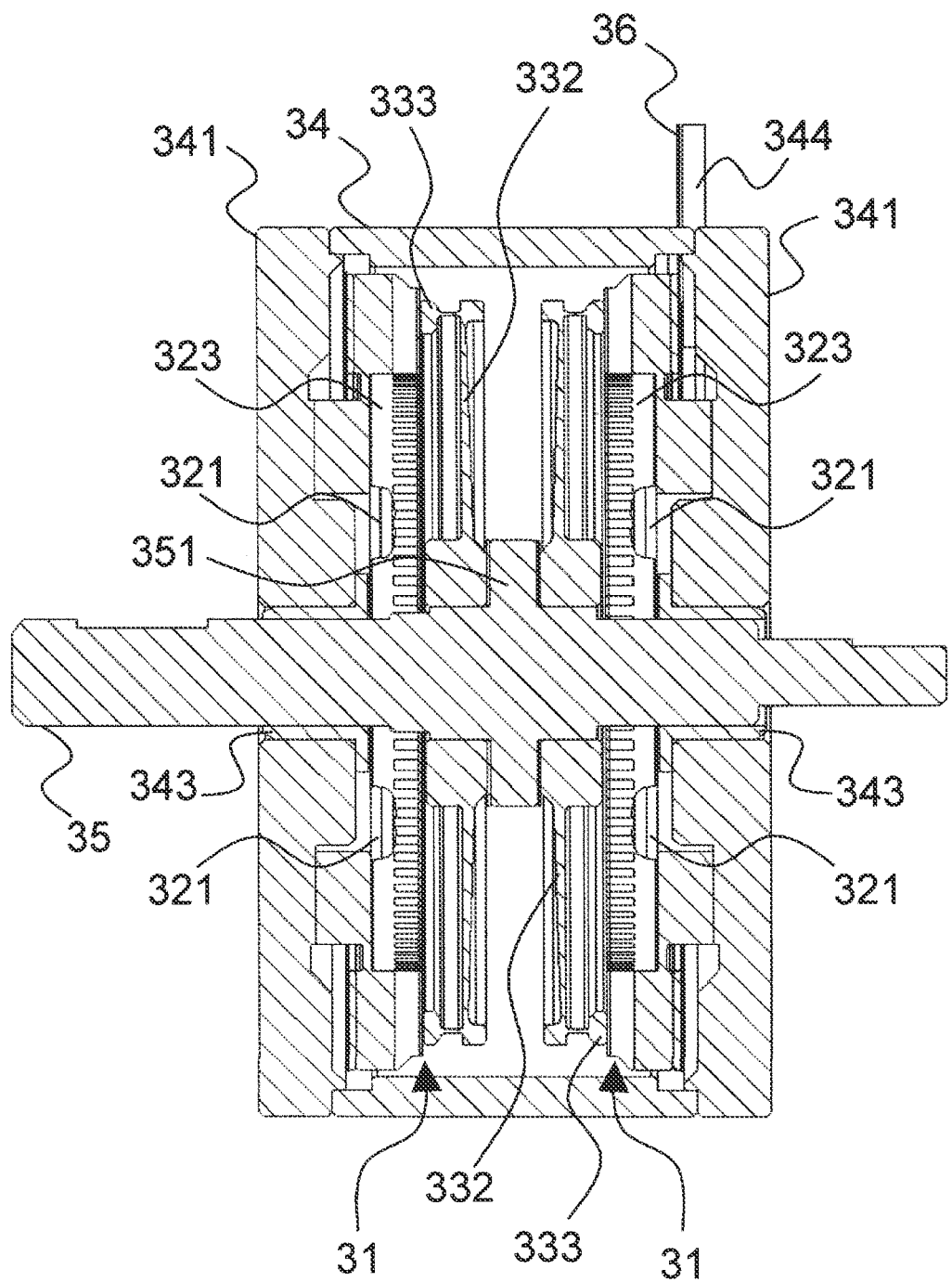
FIG. 4 is a schematic sectional view of the ultrasonic motor unit.

FIG. 3 is a schematic developed view of the ultrasonic motor unit 3 according to this embodiment. FIG. 4 is a central sectional view of the ultrasonic motor unit 3.

As illustrated in FIG. 3, the ultrasonic motor unit 3 according to this embodiment includes multiple ultrasonic motors 31 having the same configuration, which are arranged so as to be substantially bilaterally symmetric. Specifically, the ultrasonic motor unit 3 includes a first ultrasonic motor 311, and a second ultrasonic motor 312 provided coaxially with the first ultrasonic motor 311. Further, the ultrasonic motor unit 3 includes the shaft 35 passing through the first ultrasonic motor 311 and the second ultrasonic motor 312, and a case 34, to which a pair of bases 341 are fixed. The pair of bases 341 each has a plate-like shape, and is fixed to the case 34 with screws. The first ultrasonic motor 311 and the second ultrasonic motor 312 are housed in a substantially columnar space inside the case 34. Further, the first ultrasonic motor 311 and the second ultrasonic motor 312 each include a disc-like stator 32 and a disc-like rotor 33. The first ultrasonic motor 311 and the second ultrasonic motor 312 are housed in the case 34 under a state in which the first ultrasonic motor 311 and the second ultrasonic motor 312 are sandwiched between the pair of bases 341. The pair of bases 341 each have a terminal support plate 344 fixed thereto with a screw so as to mount a connector for connection to the outside.

The stator 32 includes a piezoelectric element 322, an elastic member 323, and a slide member 324 in an order from the base 341 side to the rotor 33 side. The piezoelectric element 322 and the slide member 324 are bonded to the elastic member 323. Further, a flexible substrate 36 is bonded to the stator 32, and the flexible substrate 36 and the stator 32 are electrically connected to each other. When a high frequency voltage is applied to the piezoelectric element 322 via the flexible substrate 36, flexural oscillation occurs in the elastic member 323 due to expansion and contraction of the piezoelectric element 322, and accordingly a progressive wave is generated in a circumferential direction thereof. The rotor 33 is held in contact with the elastic member 323 via the slide member 324, and hence, when the progressive wave is generated, the rotor 33 rotates in a direction opposite to that of the progressive wave. Along with the rotation, the shaft 35 rotates in the same direction as that of the rotor 33. In this embodiment, the rotation of the rotor 33 in a case of ejecting the chemical liquid is referred to as forward rotation, and the rotation of the rotor 33 in a direction opposite to the direction of the forward rotation is referred to as reverse rotation. For example, the forward rotation corresponds to the rotation of the rotor 33 in a case of moving the actuator 413 forwardly, and the reverse rotation corresponds to the rotation of the rotor 33 in a case of moving the actuator 413 backwardly. At the time of the normal control performed in accordance with the injection protocol, the normal voltage within the predetermined range is applied to the piezoelectric element 322.

As illustrated in FIG. 4, the stator 32 is fixed to the base 341 with screws 321, and the rotor 33 is fixed to a flange 351 of the shaft 35 with screws. The base 341 is provided with a hole through which the shaft 35 passes, and a bush 343 is fitted to the hole by press fitting. The bush 343 functions as a bearing for the shaft 35, and each end of the shaft 35 passes through the bush 343. The rotors 33 of the first ultrasonic motor 311 and the second ultrasonic motor 312 each include a belleville spring portion 332 having a disc-like shape. The belleville spring portion 332 functions as a spring for biasing the rotor 33 against the stator 32. The rotor 33 includes a base portion 333 held in contact with the slide member 324 of the stator 32. The belleville spring portion 332 is provided between the base portion 333 and the center of the rotor 33. The belleville spring portion 332 biases the base portion 333 against the stator 32 so that the rotor 33 comes into close contact with the stator 32. Accordingly, there is no need to separately provide a spring for bringing the rotor 33 and the stator 32 into close contact with each other, and hence the ultrasonic motor unit 3 can be downsized.

As is apparent from FIG. 3, the rotor 33 of the first ultrasonic motor 311 is arranged so as to be opposed to the rotor 33 of the second ultrasonic motor 312. That is, the first ultrasonic motor 311 and the second ultrasonic motor 312 are arranged so as to be substantially bilaterally symmetric across the flange 351 of the shaft 35. As spacers 37, for example, disc-like washers are arranged between the first ultrasonic motor 311 and the flange 351 of the shaft 35 and between the second ultrasonic motor 312 and the flange 351 of the shaft 35. Accordingly, when the thickness of the spacer 37 or the number of the spacers 37 is increased and decreased, the pressurizing force of the rotor 33 against the stator 32 can be increased and decreased with ease. Specifically, when the number of the spacers 37 is increased, the pressurizing force of the rotor 33 can be increased. As long as the rotor 33 and the stator 32 are sufficiently held into close contact with each other, the spacers 37 may be omitted.

The rotors 33 of the first ultrasonic motor 311 and the second ultrasonic motor 312 are opposed to each other. Therefore, in this embodiment, the ultrasonic motor unit 3 can be downsized as compared to a case where the rotor 33 of the first ultrasonic motor 311 and the rotor 33 of the second ultrasonic motor 312 are oriented in the same direction. Specifically, when the rotor 33 of one ultrasonic motor 31 and the stator 32 of another ultrasonic motor 31 are arranged so as to be opposed to each other, two flanges 351 need to be provided corresponding to the rotors 33 of the two ultrasonic motors 31, respectively. Further, an additional base for fixing the stator 32 needs to be provided in the case 34. As a result, the ultrasonic motor unit 3 is upsized. In contrast, according to this embodiment, the rotors 33 of the first ultrasonic motor 311 and the second ultrasonic motor 312 can be arranged on both sides of the single flange 351. Further, the base 341 for fixing the stator 32 does not need to be provided in the case 34. Therefore, the ultrasonic motor unit 3 can be downsized.

According to the ultrasonic motor unit 3 of this embodiment, two ultrasonic motors 31 are provided, and hence torque can be increased as compared to a case where a single ultrasonic motor 31 is provided alone. Therefore, the chemical liquid can be injected at a high pressure or at a high rate. Further, the rotors 33 of the first ultrasonic motor 311 and the second ultrasonic motor 312 are fixed to the single shaft 35. Therefore, even in a case where adhesion has occurred in one of the ultrasonic motors 31, the shaft 35 can be rotated by another of the ultrasonic motors 31. As a result, the rotational force of the other of the ultrasonic motors 31 is transmitted to the one of the ultrasonic motors 31 via the shaft 35. Accordingly, the adhesion occurring in the one of the ultrasonic motors 31 can be released.

In this embodiment, the injection head 2 and the control device 5 are made of a non-magnetic material so that the injection head 2 and the control device 5 can be arranged in the examination room. Specifically, the injection head 2 and the control device 5 are made of stainless steel, aluminum, plastics, brass, copper, ceramics, or the like. When the console 6 to be arranged in an operation room is made of a non-magnetic material as well, the console 6 can be arranged in the examination room. The ultrasonic motor unit 3 is made of a non-magnetic material as well. Specifically, phosphor bronze is used as a material for the elastic member 323, brass for the shaft 35, the screw 321, and the spacer 37, aluminum for the case 34, the base 341, and the rotor 33, and a fluororesin for the bush 343. Accordingly, the injector 1 is usable in the vicinity of an apparatus utilizing a magnetic field, such as a magnetic resonance imaging (MRI) apparatus. Note that, in a case where the injector 1 is installed sufficiently away from the MRI apparatus, or in a case where the injector 1 is magnetically shielded, the injection head 2 or the control device 5 may be made of a magnetic material. The injector 1 is also usable in combination with, for example, a computed tomography (CT) scanner, a positron emission tomography (PET) apparatus, a CT angiography apparatus, an MR angiography apparatus, and an angiography apparatus. In this case, the injection head 2 or the control device 5 may be made of a magnetic material.

The above-mentioned embodiment is merely an example, and for example, the injector 1 may be used for a piston 93 without the rod. Further, the injector 1 may be configured so that only one cylinder 91 is mountable or that three or more cylinders 91 are mountable. In this case, the injector 1 is provided with as many ultrasonic motor units 3 and drive mechanisms 4 as the number of the mountable cylinders 91. Further, the transmission mechanism 41 is not limited to the configuration in which the pinion gear and the screw gear are provided, and may employ various configurations as necessary. For example, the transmission mechanism 41 may have a configuration in which multiple gears including a pulley and a belt, rack and pinion gears, or a combination thereof are alternatively provided. Further, the shaft 35 of the ultrasonic motor unit 3 may be connected directly to the drive mechanism 4. Further, the ultrasonic motor unit 3 may be configured so that only one ultrasonic motor 31 is provided or that three or more ultrasonic motors 31 are provided.

First Embodiment

Figure 5:
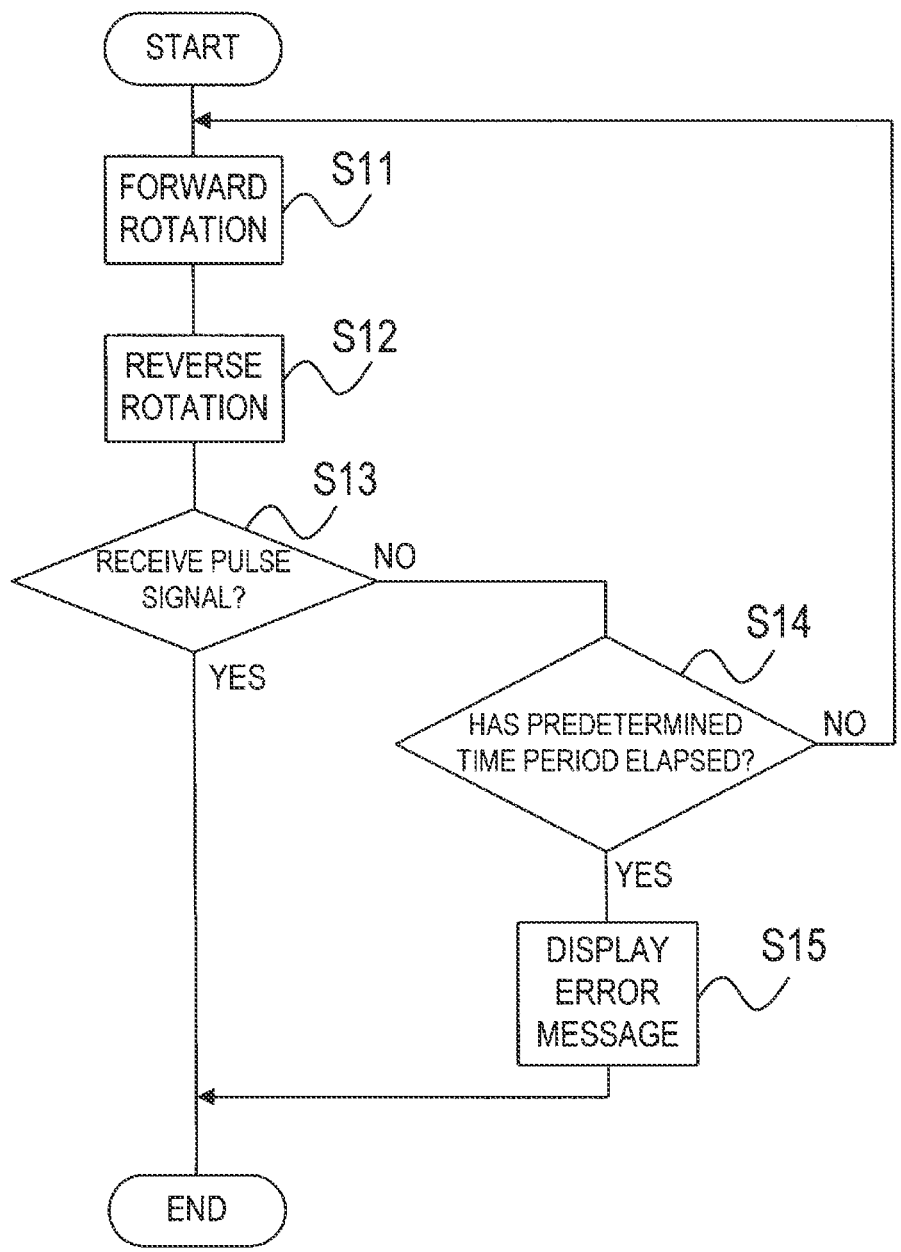
FIG. 5 is a flow chart illustrating a control method according to a first embodiment of the present invention.

FIG. 5 is a flow chart illustrating a control method for the ultrasonic motor 31 according to a first embodiment of the present invention. The control device 5 controls the ultrasonic motor 31 provided in the ultrasonic motor unit 3 for driving the drive mechanism 4, the ultrasonic motor 31 including the stator 32 and the rotor 33. In order to release the adhesion between the stator 32 and the rotor 33 of the ultrasonic motor 31, in the first embodiment, the ultrasonic motor 31 is controlled to alternately repeat the forward rotation and the reverse rotation. Specifically, the control device 5 controls the ultrasonic motor 31, that is, the first ultrasonic motor 311 and the second ultrasonic motor 312, to repeat the forward rotation and the reverse rotation. Hereinafter, the control method of the first embodiment is described with reference to the flow chart.

When the injector 1 is turned ON, the control device 5 transmits the forward rotation signal to the ultrasonic motor unit 3, and controls the ultrasonic motor unit 3 to rotate the ultrasonic motor 31 forwardly (S11). At this time, the control device 5 does not determine whether or not the adhesion has occurred. After that, the control device 5 transmits the reverse rotation signal to the ultrasonic motor unit 3, and controls the ultrasonic motor unit 3 to rotate the ultrasonic motor 31 reversely (S12). The forward rotation or the reverse rotation takes, for example, 10 msec to 50 msec, and for example, a stopping time period of approximately 10 msec to 50 msec is provided between the forward rotation and the reverse rotation. The time period of the forward rotation, the time period of the reverse rotation, and the stopping time period may be set equal to one another. Therefore, the forward rotation and the reverse rotation are repeated every several tens of milliseconds. After the forward rotation and the reverse rotation are performed, for example, a predetermined stopping time period of approximately 0.5 seconds to 1 second may be provided before the succeeding forward rotation and reverse rotation are performed. That is, when a single operation is defined as an operation in which the ultrasonic motor 31 rotates forwardly and stops thereafter, and then rotates reversely and stops again thereafter, the predetermined stopping time period can be provided until the succeeding operation (forward rotation) is started.

At the time of the forward rotation and the reverse rotation, a predetermined normal voltage equal to the normal voltage at the time of the normal control is applied to the ultrasonic motor 31. After the forward rotation and the reverse rotation are repeated multiple times, when the shaft 35 rotates, the encoder 39 transmits the pulse signal to the control device 5. When the control device 5 has received the pulse signal ("YES" in S13), the adhesion is released or the adhesion has not occurred, and hence the control device 5 finishes the adhesion releasing control. After that, the control device 5 starts the normal control in accordance with the injection protocol in response to the user's operation. On the other hand, when the adhesion has occurred and the adhesion is not released even through the adhesion releasing control, the shaft 35 does not rotate. Therefore, the encoder 39 does not transmit the pulse signal to the control device 5 ("NO" in S13). In this case, the control device 5 determines whether or not a predetermined time period has elapsed since the start of the adhesion releasing control (S14). When the control device 5 determines that the predetermined time period has not elapsed ("NO" in S14), the adhesion has occurred and the adhesion is not released, and hence the control device 5 returns to S11 to continue the adhesion releasing control. As a result, the control device 5 controls the ultrasonic motor 31 to repeat the forward rotation and the reverse rotation multiple times within the preset time period. The predetermined time period is set in advance, and for example, ranges from 5 seconds to 60 seconds. On the other hand, when the control device 5 determines that the predetermined time period has elapsed ("YES" in S14), the control device 5 displays an error message on the display 53 (S15), and finishes the adhesion releasing control. In this case, the control device 5 starts the normal control after the user releases the adhesion.

According to the first embodiment, the forward rotation and the reverse rotation are repeated within the predetermined time period, and thus forces from the forward rotation direction and the reverse rotation direction can be applied repeatedly to the stator 32 and the rotor 33 of the ultrasonic motor 31. Accordingly, the adhesion between the stator 32 and the rotor 33 can be released effectively. The control device 5 performs the adhesion releasing control for the ultrasonic motor 31 before determining whether or not the adhesion has occurred or without determining whether or not the adhesion has occurred. The control device 5 automatically performs the adhesion releasing control, and hence the user does not need to release the adhesion after the occurrence of the adhesion. Further, when the adhesion is automatically released, the step of determining the presence/absence of the adhesion by the control device 5 can be omitted.

Second Embodiment

Figure 6:
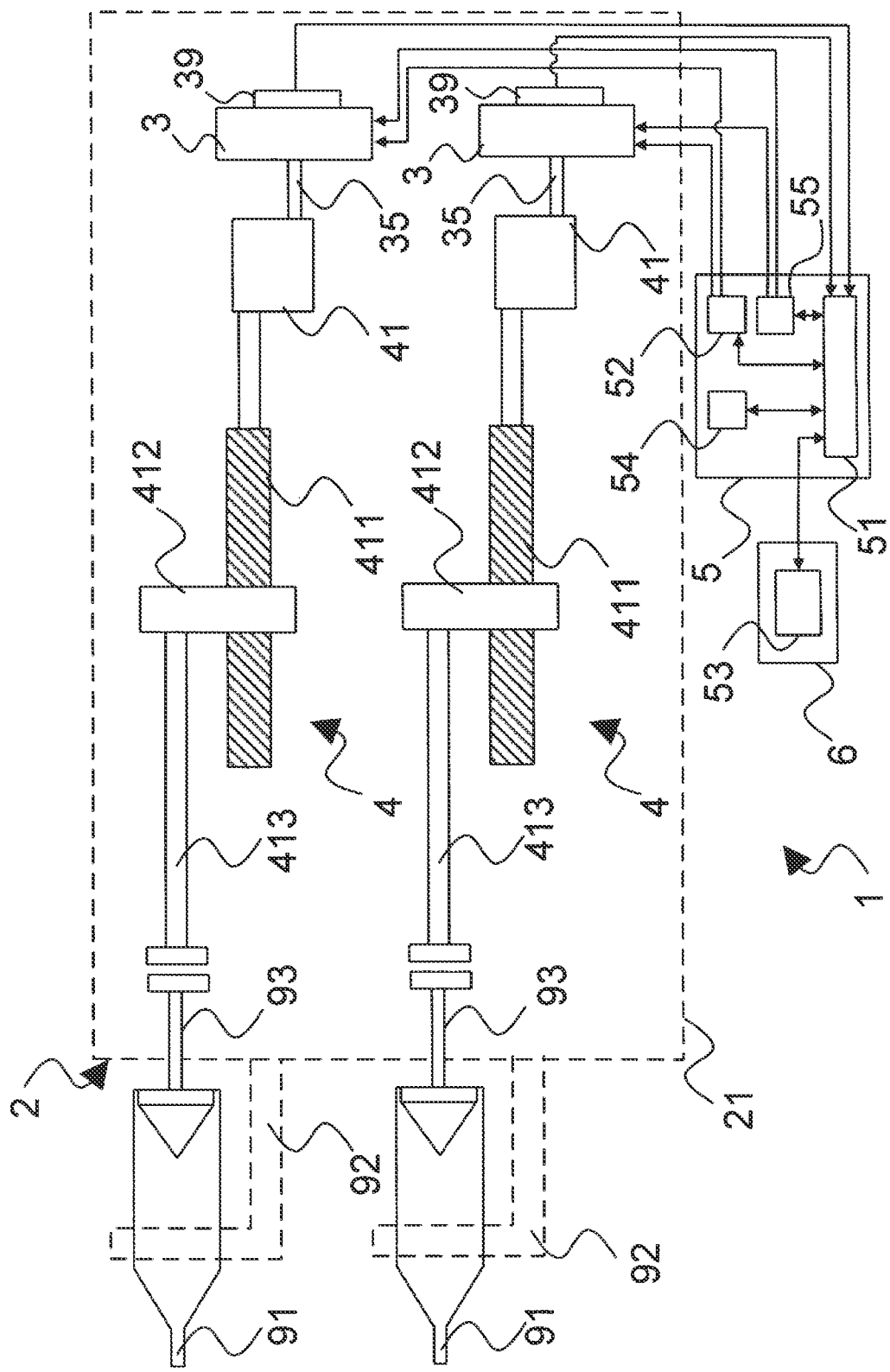
FIG. 6 is a block diagram of an injector according to a second embodiment and a third embodiment of the present invention.
Figure 7:
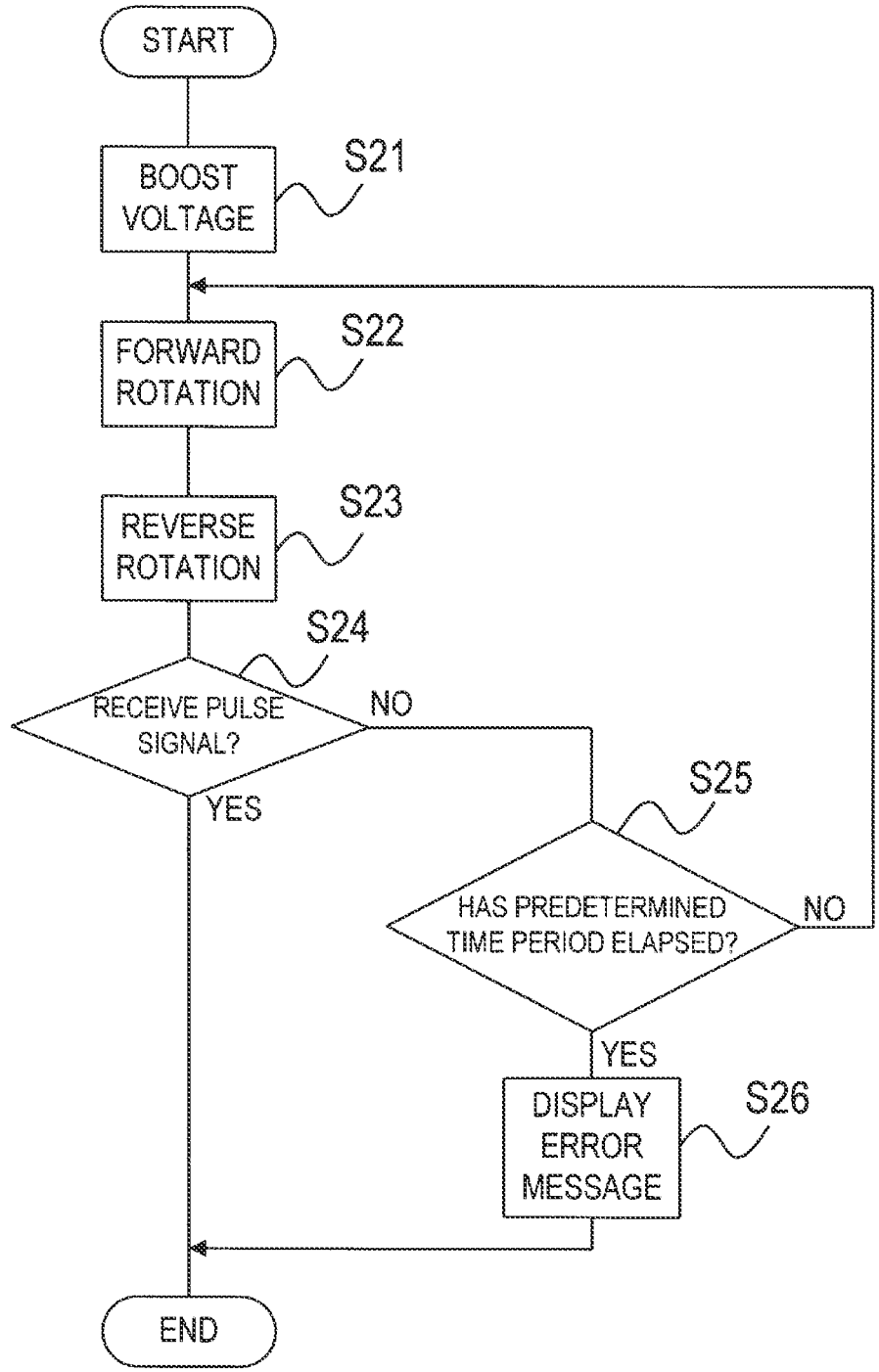
FIG. 7 is a flow chart illustrating a control method according to the second embodiment.

FIG. 6 is a block diagram of an injector 1 according to a second embodiment of the present invention. FIG. 7 is a flow chart illustrating a control method for the ultrasonic motor 31 according to the second embodiment. Unlike the first embodiment, the control device 5 of the second embodiment controls the ultrasonic motor 31 to repeat the forward rotation and the reverse rotation under a state in which a voltage higher than the preset normal voltage is applied to the ultrasonic motor 31. Therefore, the injector 1 of the second embodiment further includes a boost circuit 55. The same components as those in the first embodiment are represented by the same reference symbols, and description thereof is therefore omitted herein.

As illustrated in FIG. 6, the control device 5 of the injector 1 of the second embodiment includes the boost circuit 55 electrically connected to the ultrasonic motor unit 3. The control device 5 can switch between the drive performed by the drive circuit 52 and the drive performed by the boost circuit 55. The circuits are switched in accordance with a program previously stored in the control device 5. Alternatively, the circuits may be switched in accordance with the user's operation. Hereinafter, the control method of the second embodiment is described with reference to the flow chart of FIG. 7.

When the injector 1 is turned ON, the control device 5 switches from the drive performed by the drive circuit 52 to the drive performed by the boost circuit 55, and boosts the voltage to be applied to the ultrasonic motor 31 (S21). Then, the control device 5 transmits the forward rotation signal to the ultrasonic motor unit 3, and controls the ultrasonic motor unit 3 to rotate the ultrasonic motor 31 forwardly (S22). After that, the control device 5 transmits the reverse rotation signal to the ultrasonic motor unit 3, and controls the ultrasonic motor unit 3 to rotate the ultrasonic motor 31 reversely (S23). After the forward rotation and the reverse rotation are repeated multiple times, when the shaft 35 rotates, the encoder 39 transmits the pulse signal to the control device 5. When the control device 5 has received the pulse signal ("YES" in S24), the adhesion is released or the adhesion has not occurred, and hence the control device 5 finishes the adhesion releasing control. After that, the control device 5 switches to the drive performed by the drive circuit 52 (drops the voltage), and starts the normal control in response to the user's operation.

When the adhesion has occurred and the adhesion is not released even through the adhesion releasing control, the shaft 35 does not rotate. Therefore, the encoder 39 does not transmit the pulse signal to the control device 5 ("NO" in S24). In this case, the control device 5 determines whether or not a predetermined time period has elapsed since the start of the adhesion releasing control (S25). When the control device 5 determines that the predetermined time period has not elapsed ("NO" in S25), the adhesion has occurred and the adhesion is not released, and hence the control device 5 returns to S22 to continue the adhesion releasing control. On the other hand, when the control device 5 determines that the predetermined time period has elapsed ("YES" in S25), the control device 5 displays an error message on the display 53 (S26), and finishes the adhesion releasing control. In this case, the control device 5 starts the normal control after the user releases the adhesion.

Also in the second embodiment, the forward rotation and the reverse rotation are repeated within the predetermined time period, and thus the forces from the forward rotation direction and the reverse rotation direction can be applied repeatedly to the stator 32 and the rotor 33 of the ultrasonic motor 31. Accordingly, the adhesion between the stator 32 and the rotor 33 can be released effectively. When the adhesion is automatically released, the user does not need to release the adhesion after the occurrence of the adhesion, and the step of determining the presence/absence of the adhesion by the control device 5 can be omitted as well. Moreover, through the application of the high voltage, the drive torque of the ultrasonic motor 31 can be increased. Accordingly, forces greater than in the first embodiment can be applied to the stator 32 and the rotor 33, and hence the adhesion can be released more effectively.

Third Embodiment

Figure 8:
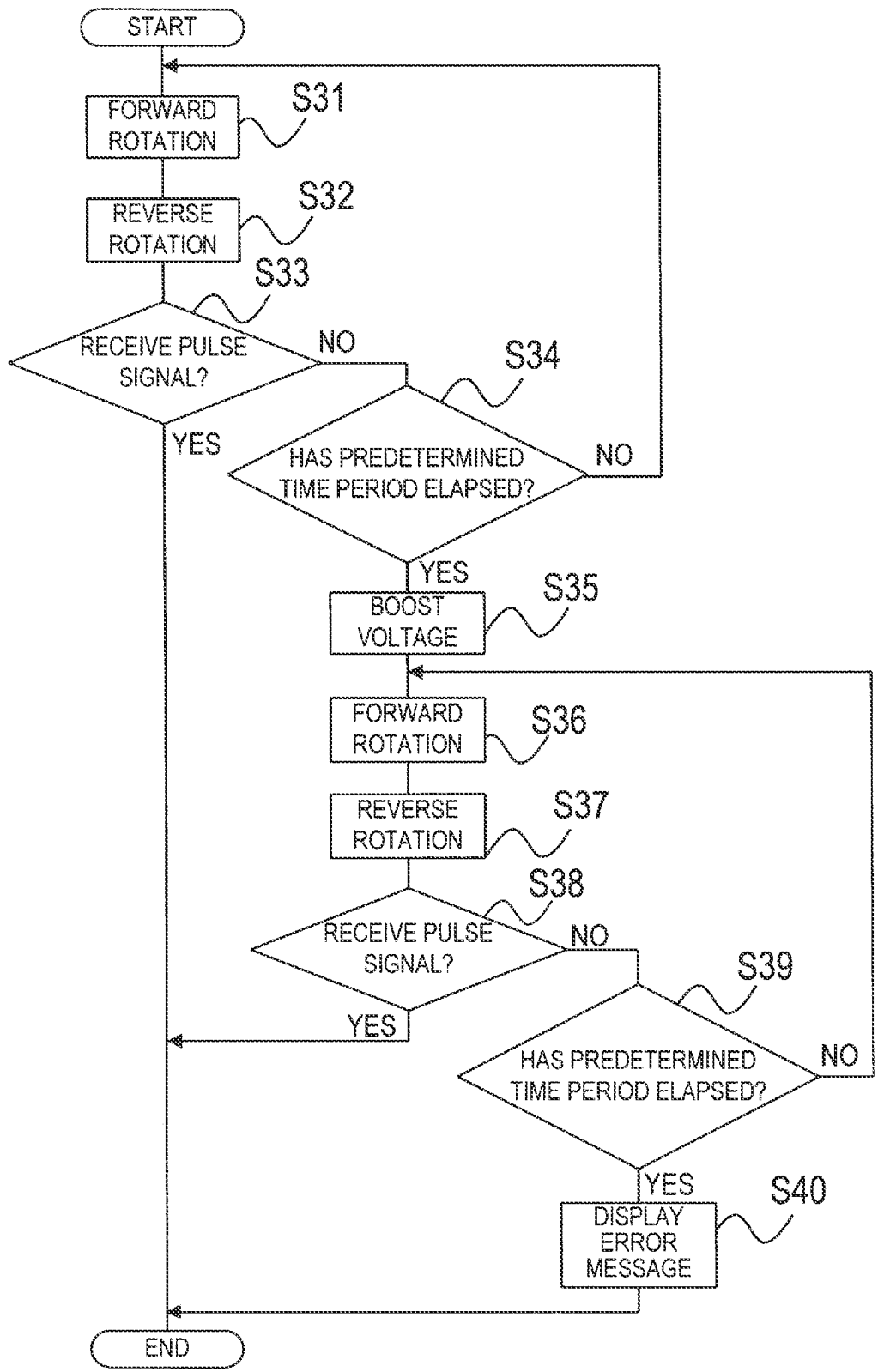
FIG. 8 is a flow chart illustrating a control method according to the third embodiment.

FIG. 8 is a flow chart illustrating a control method for the ultrasonic motor 31 according to a third embodiment of the present invention. Unlike the second embodiment, the control device 5 of the third embodiment controls the ultrasonic motor 31 to repeat the forward rotation and the reverse rotation under a state in which a voltage higher than the normal voltage is applied to the ultrasonic motor 31, after the ultrasonic motor 31 has repeated the forward rotation and the reverse rotation under a state in which the preset normal voltage is applied to the ultrasonic motor 31. Therefore, the injector 1 of the third embodiment includes the boost circuit 55 similarly to the second embodiment. Hereinafter, the control method of the third embodiment is described with reference to the flow chart.

When the injector 1 is turned ON, the control device 5 transmits the forward rotation signal to the ultrasonic motor unit 3, and controls the ultrasonic motor unit 3 to rotate the ultrasonic motor 31 forwardly (S31). After that, the control device 5 transmits the reverse rotation signal to the ultrasonic motor unit 3, and controls the ultrasonic motor unit 3 to rotate the ultrasonic motor 31 reversely (S32). At the time of the first forward rotation and the first reverse rotation, the preset normal voltage equal to the normal voltage at the time of the normal control is applied to the ultrasonic motor 31. After the forward rotation and the reverse rotation are repeated multiple times, when the shaft 35 rotates, the encoder 39 transmits the pulse signal to the control device 5. When the control device 5 has received the pulse signal ("YES" in S33), the adhesion is released or the adhesion has not occurred, and hence the control device 5 finishes the adhesion releasing control. After that, the control device 5 starts the normal control in accordance with the injection protocol in response to the user's operation.

When the adhesion has occurred and the adhesion is not released even through the adhesion releasing control, the shaft 35 does not rotate. Therefore, the encoder 39 does not transmit the pulse signal to the control device 5 ("NO" in S33). In this case, the control device 5 determines whether or not a predetermined time period has elapsed since the start of the adhesion releasing control (S34). When the control device 5 determines that the predetermined time period has not elapsed ("NO" in S34), the adhesion has occurred and the adhesion is not released, and hence the control device 5 returns to S31 to continue the adhesion releasing control. On the other hand, when the control device 5 determines that the predetermined time period has elapsed ("YES" in S34), the control device 5 switches from the drive performed by the drive circuit 52 to the drive performed by the boost circuit 55, and boosts the voltage to be applied to the ultrasonic motor 31 so that the second forward rotation and the second reverse rotation are performed under a state in which the voltage is boosted (S35). The predetermined time period is set in advance, and for example, ranges from 5 seconds to 60 seconds. Then, the control device 5 transmits the forward rotation signal to the ultrasonic motor unit 3, and controls the ultrasonic motor unit 3 to rotate the ultrasonic motor 31 forwardly (S36). After that, the control device 5 transmits the reverse rotation signal to the ultrasonic motor unit 3, and controls the ultrasonic motor unit 3 to rotate the ultrasonic motor 31 reversely (S37).

After the second forward rotation and the second reverse rotation are repeated multiple times, when the shaft 35 rotates, the encoder 39 transmits the pulse signal to the control device 5. When the control device 5 has received the pulse signal ("YES" in S38), the adhesion is released, and hence the control device 5 finishes the adhesion releasing control. After that, the control device 5 switches to the drive performed by the drive circuit 52 (drops the voltage), and starts the normal control in response to the user's operation. On the other hand, when the adhesion is not released, the shaft 35 does not rotate, and hence the encoder 39 does not transmit the pulse signal to the control device 5 ("NO" in S38). In this case, the control device 5 determines whether or not a predetermined time period has elapsed since the start of the adhesion releasing control (S39). When the control device 5 determines that the predetermined time period has not elapsed ("NO" in S39), the adhesion is not released, and hence the control device 5 returns to S36 to continue the adhesion releasing control. This predetermined time period is also set in advance, and for example, ranges from 5 seconds to 60 seconds. On the other hand, when the control device 5 determines that the predetermined time period has elapsed ("YES" in S39), the control device 5 displays an error message on the display 53 (S40), and finishes the adhesion releasing control. In this case, the control device 5 starts the normal control after the user releases the adhesion.

Also in the third embodiment, the forward rotation and the reverse rotation are repeated within the predetermined time period, and thus the forces from the forward rotation direction and the reverse rotation direction can be applied repeatedly to the stator 32 and the rotor 33 of the ultrasonic motor 31. Accordingly, the adhesion between the stator 32 and the rotor 33 can be released effectively. When the adhesion is automatically released, the user does not need to release the adhesion after the occurrence of the adhesion, and the step of determining the presence/absence of the adhesion by the control device 5 can be omitted as well. Moreover, when the adhesion cannot be released, the second forward rotation and the second reverse rotation are repeated under the state in which the high voltage is applied. Accordingly, forces greater than in the first embodiment can be applied to the stator 32 and the rotor 33, and hence the adhesion can be released more effectively.

In the second embodiment and the third embodiment, the boost circuit 55 is provided to the control device 5. Alternatively, the boost circuit 55 may be provided to the console 6. Still alternatively, the boost circuit 55 may be provided to the injection head 2.

Fourth Embodiment

Figure 9:
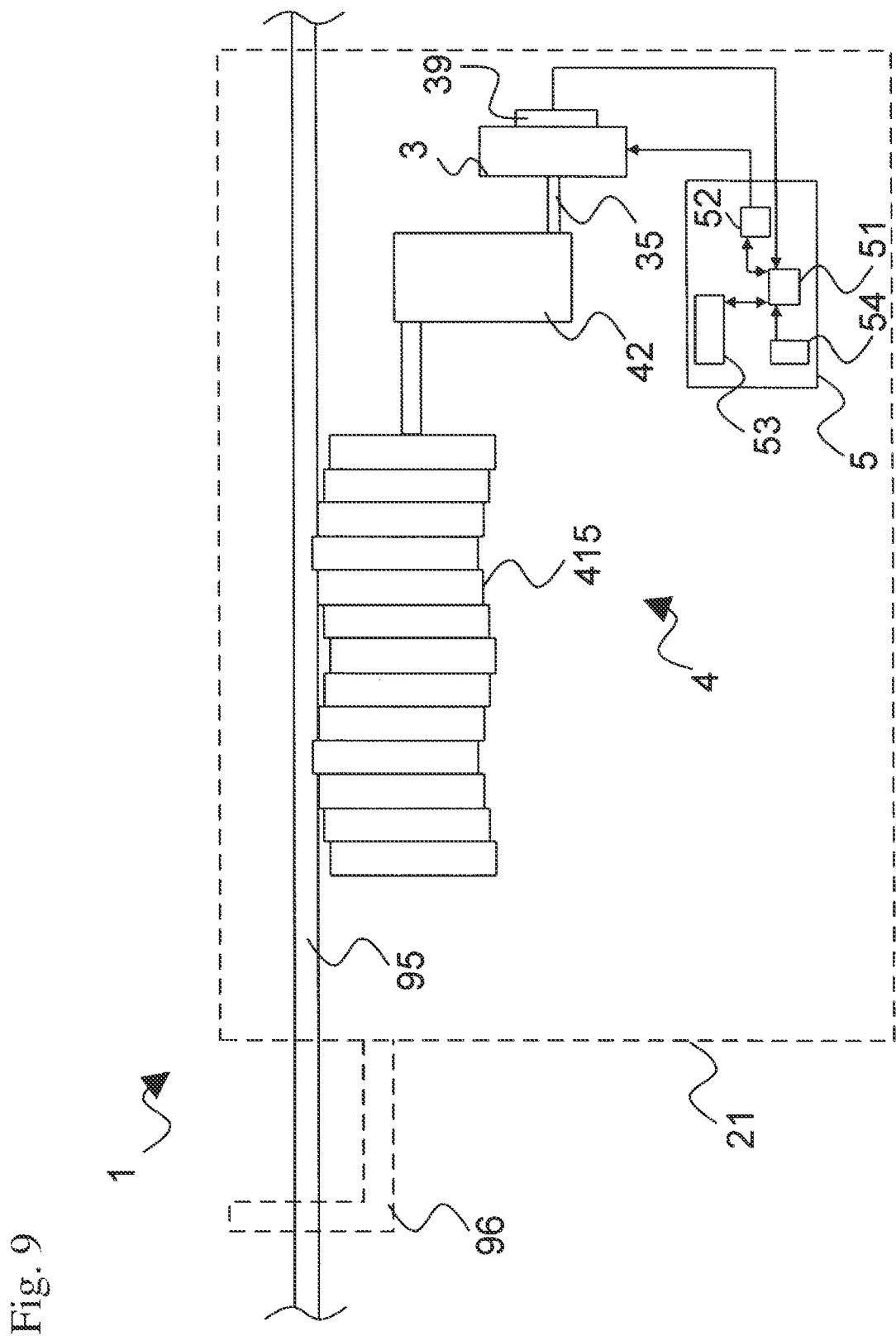
FIG. 9 is a block diagram of an injector according to a fourth embodiment of the present invention.

FIG. 9 is a block diagram of an injector 1 according to a fourth embodiment of the present invention. The injector 1 of the fourth embodiment also includes the ultrasonic motor unit 3 including the ultrasonic motor 31, the drive mechanism 4 to be driven by the ultrasonic motor unit 3, and the control device 5 for controlling the ultrasonic motor unit 3. Unlike the above-mentioned embodiments, the drive mechanism 4 of the fourth embodiment includes a peristaltic finger mechanism 415, and the peristaltic finger mechanism 415 is connected to a transmission mechanism 42 that is connected to the shaft 35 of the ultrasonic motor 31. The same components as those in each of the above-mentioned embodiments are represented by the same reference symbols, and description thereof is therefore omitted herein.

In the fourth embodiment, the control device 5 is arranged inside the frame 21. Further, the control device 5 includes the drive circuit 52, and is electrically connected to the ultrasonic motor unit 3 so as to transmit the drive signal thereto. The frame 21 includes a tube holder 96, and the tube holder 96 holds a tube 95, through which the chemical liquid flows. The drive mechanism 4 includes the transmission mechanism 42 for transmitting the rotation from the ultrasonic motor unit 3, and the peristaltic finger mechanism 415 connected to the transmission mechanism 42. The transmission mechanism 42 includes a pulley and a belt. The rotation of the shaft 35 of the ultrasonic motor unit 3 is transmitted to the peristaltic finger mechanism 415 via the pulley and the belt. When the shaft 35 rotates forwardly, the peristaltic finger mechanism 415 rotates forwardly in accordance with the transmitted rotation. The tube 95 is made of a flexible material, such as vinyl chloride having a high elasticity, and hence has such a property that the tube 95 is restored even when being pressed. Therefore, when the peristaltic finger mechanism 415 rotates forwardly, the tube 95 is sequentially pressed, and the chemical liquid is ejected from the tube 95. The chemical liquid is injected into the body of a patient via such as a catheter connected to a distal end of the tube 95. Also in the fourth embodiment, the rotation of the rotor 33 of the ultrasonic motor 31 in a case of ejecting the chemical liquid is referred to as forward rotation, and the rotation of the rotor 33 in a direction opposite to the direction of the forward rotation is referred to as reverse rotation.

Also in the fourth embodiment, the adhesion releasing control of each of the above-mentioned embodiments can be performed. Therefore, the forward rotation and the reverse rotation are repeated within the predetermined time period, and thus the forces from the forward rotation direction and the reverse rotation direction can be applied repeatedly to the stator 32 and the rotor 33 of the ultrasonic motor 31. Accordingly, the adhesion between the stator 32 and the rotor 33 can be released effectively. The control device 5 automatically performs the adhesion releasing control, and hence the user does not need to release the adhesion after the occurrence of the adhesion. Further, when the adhesion is automatically released, the step of determining the presence/absence of the adhesion by the control device 5 can be omitted.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions. Further, the embodiments and modifications may be combined as appropriate without departing from the scope of the present invention.

For example, in the adhesion releasing control of each of the above-mentioned embodiments, the reverse rotation is performed after the forward rotation, but alternatively, the forward rotation may be performed after the reverse rotation. Also in this case, the forces from the forward rotation direction and the reverse rotation direction can be applied repeatedly to the stator 32 and the rotor 33 of the ultrasonic motor 31. Accordingly, the adhesion between the stator 32 and the rotor 33 can be released effectively. Further, the adhesion releasing control may be performed at a timing other than the timing at which the injector 1 is turned ON. For example, the adhesion releasing control may be performed at a timing at which the drive signal is transmitted to the ultrasonic motor unit 3. In this case, the adhesion releasing control is performed before the drive of the ultrasonic motor 31 (forward rotation or reverse rotation) is started. Further, the adhesion releasing control may be performed in response to the user's operation. In this case, there may be employed a configuration in which the operation unit of the injection head 2 is provided with an adhesion releasing button, or a configuration in which an adhesion releasing button is displayed on the touch panel. Further, the adhesion releasing control may be performed when the actuator 413 is moved backwardly, that is, at a timing at which the reverse rotation signal is transmitted to the ultrasonic motor unit 3.

In the adhesion releasing control of each of the above-mentioned embodiments, it is determined whether or not to display the error message based on whether or not the predetermined time period has elapsed. Alternatively, it may be determined whether or not to display the error message based on whether or not the number of times of the forward rotation and the reverse rotation of the ultrasonic motor 31 has reached a predetermined number. Further, the injector 1 of the present invention is not limited to the configuration in which the injector 1 is connected to the external power supply, and may employ a configuration utilizing a wireless power supply, or a configuration in which an internal power supply such as a battery is provided.

This application claims priority from Japanese Patent Application No. 2011-132031 filed on Jun. 14, 2011, which is hereby incorporated by reference herein.

The invention claimed is:

1. An ultrasonic motor unit comprising:
a single shaft; and
a first ultrasonic motor and a second ultrasonic motor respectively including a stator which includes a piezoelectric element and a rotor which comes into close contact with the stator so as not to rotate when a voltage is not applied to the first and second ultrasonic motors respectively,
wherein the rotor of the first ultrasonic motor and the rotor of the second ultrasonic motor are fixed to the single shaft so as to transmit, when one of the first ultrasonic motor and the second ultrasonic motor fixed to the single shaft is adhered, rotational force of another one of the first ultrasonic motor and the second ultrasonic motor fixed to the single shaft via the single shaft to rotate the rotor of the one of the first ultrasonic motor and the second ultrasonic motor.

2. The ultrasonic motor unit according to claim 1, wherein a flange is formed on the single shaft, each of the rotor of the first ultrasonic motor and the rotor of the second ultrasonic motor is respectively in contact with each of the stator of the first ultrasonic motor and the stator of the second ultrasonic motor, and the rotor of the first ultrasonic motor opposes the rotor of the second ultrasonic motor with the flange being disposed therebetween.

3. The ultrasonic motor unit according to claim 2, further comprising:
a spacer arranged between the rotor of the first ultrasonic motor and the flange or between the rotor of the second ultrasonic motor and the flange.

4. The ultrasonic motor unit according to claim 1, further comprising:
a connector provided on each of the first ultrasonic motor and the second ultrasonic motor for connection to outside.

5. The ultrasonic motor unit according to claim 1, further comprising:
a flexible substrate electrically connected to one of the stator of the first ultrasonic motor and the stator of the second ultrasonic motor, and having a ring-shaped portion and a protruding portion which protrudes outward from an outer circumference of the ring-shaped portion.

6. The ultrasonic motor unit according to claim 5, further comprising:
a terminal support plate which is provided on each of the first ultrasonic motor and the second ultrasonic motor, on which a connector for connection to outside is mounted, and which is in contact with the protruding portion of the flexible substrate.

7. An injector which injects a chemical liquid, the injector comprising:
the ultrasonic motor unit according to claim 1;

a drive mechanism to be driven by the ultrasonic motor unit; and a control device controlling the first ultrasonic motor and the second ultrasonic motor of the ultrasonic motor unit.

8. The injector according to claim 7, wherein the control device controls the first ultrasonic motor and the second ultrasonic motor to alternately repeat forward rotation and reverse rotation to release adhesion between the stator and the rotor.

* * * * *